(12) United States Patent
Astier et al.

(10) Patent No.: US 10,591,440 B2
(45) Date of Patent: Mar. 17, 2020

(54) TUNNEL JUNCTIONS IN MICROFLUIDIC ARRAYS FOR MOLECULAR RECOGNITION

(71) Applicant: Roche Sequencing Solutions, Inc., Pleasanton, CA (US)

(72) Inventors: Yann Astier, Livermore, CA (US); Juraj Topolancik, Redwood City, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 316 days.

(21) Appl. No.: 15/661,931

(22) Filed: Jul. 27, 2017

(65) Prior Publication Data

US 2018/0031523 A1 Feb. 1, 2018

Related U.S. Application Data

(60) Provisional application No. 62/369,704, filed on Aug. 1, 2016.

(51) Int. Cl.
*G01N 27/447* (2006.01)
*G01N 27/28* (2006.01)
(Continued)

(52) U.S. Cl.
CPC .... *G01N 27/44791* (2013.01); *B01L 3/50273* (2013.01); *B01L 3/502715* (2013.01);
(Continued)

(58) Field of Classification Search
CPC ............ G01N 27/44791; G01N 27/28; G01N 27/307; G01N 27/403; G01N 27/447;
(Continued)

(56) References Cited

U.S. PATENT DOCUMENTS

| 2003/0217934 | A1 | 11/2003 | Hodges et al. |
| 2012/0160679 | A1* | 6/2012 | Suda ................. G01N 27/307 204/406 |

(Continued)

FOREIGN PATENT DOCUMENTS

WO 2015/161119 A1 10/2015

OTHER PUBLICATIONS

Batzer, et al., "Enhanced evolutionary PCR using oligonucleotides with inosine at the 3'-terminus", (1991), Oxford University Press, Nucleic Acids Research, vol. 19, No. 18, p. 5081.

(Continued)

*Primary Examiner* — Susan D Leong
(74) *Attorney, Agent, or Firm* — Kilpatrick Townsend and Stockton LLP

(57) ABSTRACT

Embodiments of the present technology include a system for analyzing a molecule. The system may include a device. The device includes a first conductive element, a second conductive element, and an insulating layer. The insulating layer may be tapered in a direction to reach a minimum thickness at a first end of the device. The insulating layer is disposed between the first conductive element and the second conductive element. The device may include a voltage source in electrical communication with the first conductive element and the second conductive element. The device may also include an electrical meter in electrical communication with the voltage source, the first conductive element, and the second conductive element.

12 Claims, 15 Drawing Sheets

(51) Int. Cl.

| | |
|---|---|
| G01N 33/487 | (2006.01) |
| G01N 27/327 | (2006.01) |
| B01L 3/00 | (2006.01) |
| H01L 43/02 | (2006.01) |
| H01L 43/10 | (2006.01) |
| H01L 43/12 | (2006.01) |

(52) U.S. Cl.
CPC ... *G01N 27/3278* (2013.01); *G01N 33/48721* (2013.01); *H01L 43/02* (2013.01); *H01L 43/10* (2013.01); *H01L 43/12* (2013.01); *B01L 2300/0645* (2013.01); *B01L 2300/0887* (2013.01); *B01L 2400/0421* (2013.01)

(58) Field of Classification Search
CPC .......... B01L 3/502715; B01L 3/50273; B01L 2300/0887; B01L 2300/0421
See application file for complete search history.

(56) References Cited

U.S. PATENT DOCUMENTS

| | | | |
|---|---|---|---|
| 2015/0001099 A1 | 1/2015 | Bai et al. | |
| 2017/0038369 A1* | 2/2017 | Lindsay | ............ G01N 33/5438 |

OTHER PUBLICATIONS

Ohtsuka et al., "An Alternative Approach to Deoxyoligonucleotides as Hybridization Probes by Insertion of Deoxylnosine at Ambiguous Codon Positions" (1985), The Journal of Biological Chemistry, vol. 260. No. 5, pp. 2605-2608.

Rossolini et al., Use of deoxyinosine-containing primers vs degenerate primers for polymerase chain reaction based on ambiguous sequence information, Molecular and Cellular Probes, (1994), pp. 91-98, vol. 8.

Partial International Search Report dated Oct. 30, 2017 2017 in corresponding International Application No. PCT/EP2017/069307 (10 pages).

Tyagi, P. et al.; "Advantages of Prefabricated Tunnel Junction-Based Spintronics Devices"; *NANO: Brief Reports and Reviews*; vol. 10, No. 4; 1530002; 2015; 22 pages.

Wang, C., et al.; "Clog-free translocation of long DNA in nanofluidic pillar arrays and 30 nm wide channels: A fabrication and hydrodynamic study"; *18th International Conference on Miniaturized Systems for Chemistry and Life Sciences, MicroTAS 2014*; pp. 1347-1349; 2014; Chemical and Biological Microsystems Society.

Zhao, W. et al., "Failure Analysis in Magnetic Tunnel Junction Nanopillar with Interfacial Perpendicular Magnetic Anisotropy"; *Materials*; vol. 9, No. 41; 2016; 17 pages.

* cited by examiner

TUNNEL JUNCTIONS IN MICROFLUIDIC ARRAYS FOR MOLECULAR RECOGNITION

CROSS-REFERENCES TO RELATED APPLICATIONS

This application claims priority to U.S. Provisional Application No. 62/369,704, filed Aug. 1, 2016, which is incorporated herein by reference in its entirety for all purposes.

FIELD

This application relates to methods and systems to analyze molecules using tunnel junctions. Such analysis of molecules can include sequencing biological polymers, such as nucleic acids.

BACKGROUND

Possible technologies for analyzing single molecules (e.g. nucleic acids) include tunneling junction devices that have a sub-molecular sized gap between two electrodes. When the molecule makes contact with the two electrode, the molecule may create a tunneling current. The tunneling current can be analyzed to identify a portion of the molecule. Dimensions of the gap may be on the order of nanometers, including less than 2 nm, or even sub-nanometer. Creating a gap of this size may require precise and expensive techniques. Toolsets and processes for tunnel junctions have been developed by magnetic recording media industry to manufacture magnetic junctions for hard-drives and non-volatile memory devices that are currently under development (W. Zhao, et al., "Failure Analysis in Magnetic Tunnel Junction Nanopillar with Interfacial Perpendicular Magnetic Anisotropy," *Materials*, Vol. 9, 41, 2016; P. Tyagi, E. Friebe, and C. Baker, "Advantages of Prefabricated Tunnel Junction-Based Spintronic s Devices," *NANO: Brief Reports and Reviews*, Vol. 10, 1530002, 2015).

Devices with such a small gap between electrodes may be subject to device failure, such as electrical shorts. Furthermore, maintaining such a thin layer between two electrodes is difficult. Improvements in the design and manufacturability of tunneling junction devices are still needed, particularly for analyzing single molecules. Ideally, design and manufacturability improvements should not come at the expense of accurate and precise analysis. These and other issues are addressed by the technology described in this document.

BRIEF SUMMARY

Embodiments of the present technology may allow for the analysis of molecules (e.g., sequencing of nucleic acid molecules) by tunneling recognition at a tunneling junction. A tunneling junction of the present technology can include an insulating layer between two electrodes. A voltage may be applied to the electrodes. When a molecule makes contact with both electrodes, the molecule allows current to tunnel through the molecule. The characteristics of the current may aid in identifying a portion of the molecule, for example, a particular nucleotide or base present in a nucleic acid molecule.

Embodiments of the present technology may also allow for repeated tunneling current measurements or other electrical characteristic measurements of molecules across multiple tunneling junctions. The contact point of the electrodes with the molecule can be oriented so that the molecule can move to another tunneling junction device and make contact with the electrodes of that device. The tunneling direction may then be parallel with the substrate instead of orthogonal to the substrate. In this orientation, an electric field or a pressure gradient across the substrate can move molecules to be analyzed from one tunneling junction to another tunneling junction. A molecule can then make contact with multiple tunneling junctions, including hundreds, thousands, or tens of thousands of tunneling junctions. As a result, better statistics can be developed to identify the molecule or a portion of the molecule.

In some embodiments, the insulating layer may be tapered so that the minimum thickness is the closest part of the insulating layer to the molecule when the molecule contacts the electrodes. The minimum thickness may be on the order of nanometers or even sub-nanometer. By having an increased thickness at other portions of the insulating layer, the current or other electrical characteristic signature from the molecule can be easier to detect, as fewer electrons will tunnel through thicker portions of the insulating layer. In addition, thicker portions of the insulating layer may be less likely to have defects or allow electrical shorts. Furthermore, a tapered insulating layer may also be easier to manufacture than an insulating layer having a uniform thickness on the nanometer scale.

In some embodiments, tunneling junction devices may be oriented to form a flow channel such that a molecule may flow through the flow channel as a substantially linear or uncoiled molecule. A molecule may flow against the electrode of a first tunneling junction device and then move toward the electrode of a second tunneling junction device. The orientation of these devices forces the molecule to move in a way that prevents the molecule from coiling and allows for the molecule to contact multiple devices and register a tunneling current or other electrical characteristic with each device.

A better understanding of the nature and advantages of embodiments of the present invention may be gained with reference to the following detailed description and the accompanying drawings.

Definitions

The term "contacting" may refer to bringing one object in proximity to another object such that electrons may tunnel from one object through the other object. At a subatomic level, two objects may never physically touch each other as repulsive forces from electron clouds in the objects may prevent the objects from coming into closer proximity.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "electrical characteristic" may be understood to refer to any property related to an electrical circuit. Electrical characteristic may refer to voltage, current, resistance, impedance, inductance, or capacitance, and time variations thereof (e.g., current frequency).

DETAILED DESCRIPTION

Conventional tunneling junction devices used commercially in the magnetic recording media industry are not suitable for tunneling recognition analysis of molecules, including nucleic acids and other biological polymers. Biological polymers may include DNA, RNA, cDNA, mRNA, oligonucleotide, polynucleotide, amino acids, proteins, polypeptides, carbohydrates, and/or lipids. Conventional tunneling junction devices in the magnetic recording media industry may also not be suitable for tunneling recognition because the tunneling junctions are not oriented to allow for repeated contact with and measurements of a molecule.

I. Tunneling Junctions in Magnetic Media Industry

Figure 1:
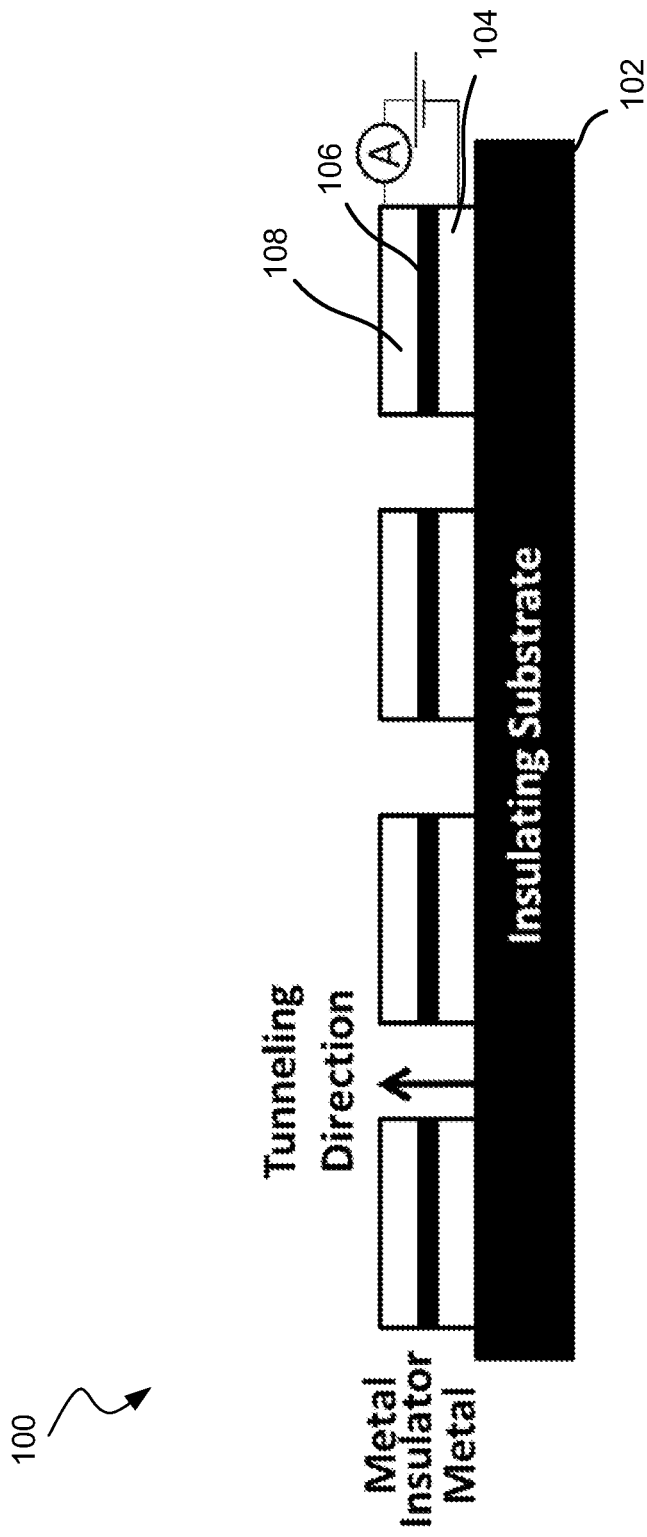
FIG. 1 shows a system of conventional vertical tunnel junctions.

FIG. 1 shows a system 100 of conventional tunneling junction devices used commercially in the magnetic media industry. A device is fabricated on an insulating substrate 102. The device includes a first metal layer 104. An insulating layer 106 is on top of first metal layer 104. A second metal layer 108 is on top of insulating layer 106. This configuration may be convenient to fabricate, but the configuration is not ideal for analyzing molecules.

To generate a tunneling current, a molecule would have to contact the first metal layer 104 and the second metal layer 108, which are stacked vertically. As a result, the tunneling direction is vertical, as viewed in FIG. 1. The molecule, traveling along the tunneling direction, would contact only a single device and not contact multiple devices. Hence, a molecule may generate only one current measurement in FIG. 1, rather than multiple current measurements. The current measurements may be noisy because the magnitude of the current measurement may be on the order of tens to hundreds of picoamps and because the molecule may not adequately contact the devices at all portions of interest (e.g., for every nucleotide of a nucleic acid). Increasing the number of measurements for a molecule will help provide more greater accuracy for analyzing the molecule, but FIG. 1 cannot consistently provide repeatable measurements of a molecule. As a result, these conventional tunneling junction devices may not allow for an accurate and reliable method for analyzing nucleic acids or other molecules.

II. Orientation and Tapering of Tunneling Junction Device

Figure 2:
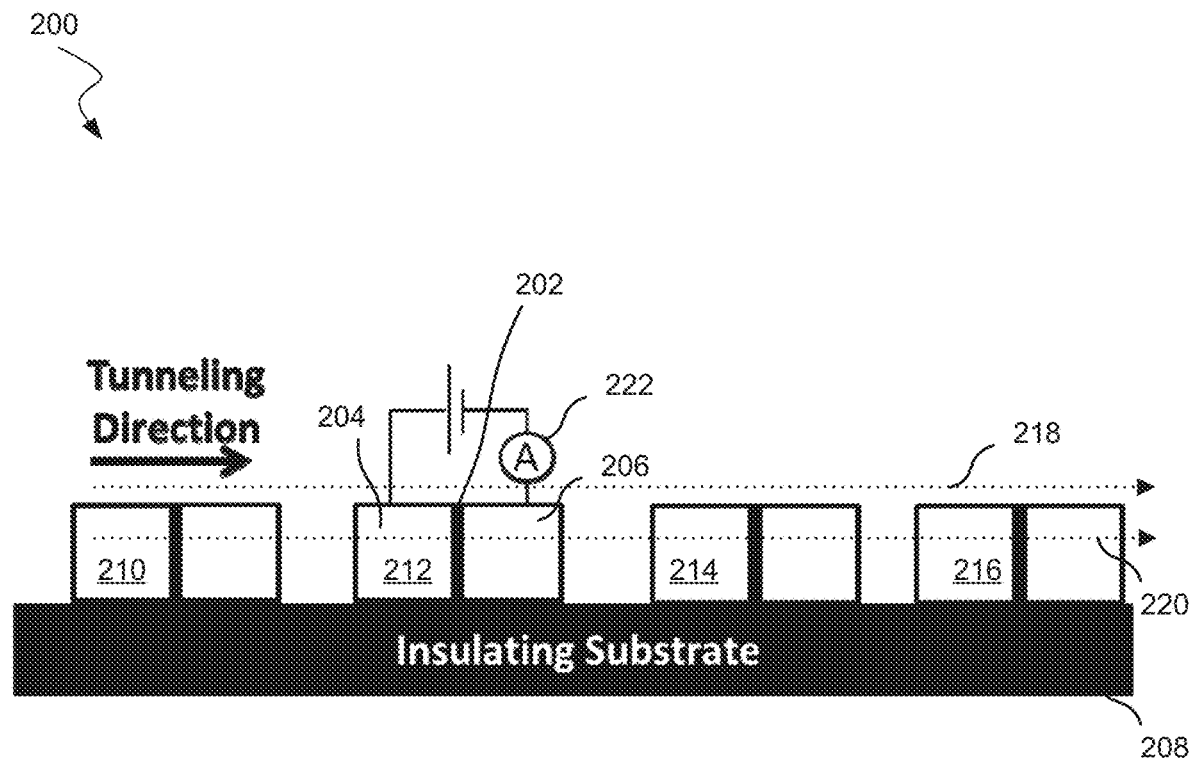
FIG. 2 shows a system of tunneling junctions according to embodiments of the present technology.

FIG. 2 shows a system 200 of tunneling junction devices according to embodiments of the present technology. An insulating layer 202 is between a first metal layer 204 and a second metal layer 206. Unlike FIG. 1, all three layers are in contact with an insulating substrate 208. As a result, the tunneling direction is horizontal, as viewed in FIG. 2. With a horizontal tunneling direction, a molecule can contact multiple devices 210, 212, 214, and 216 along insulating substrate 208.

The tunneling junction may be oriented such that the side contacting the molecule to be analyzed is on the side of the device opposite the insulating structure (e.g., in FIG. 2, toward the top of the figure). With this orientation, the path of a molecule that moves from left to right in FIG. 2 along the tops of the devices 210, 212, 214, and 216 may generate a tunneling current in the multiple devices. This possible path of a molecule along the tops of the devices in FIG. 2 is shown by the dotted arrow 218. A current meter 222 is shown, but current meter 222 may be a voltage meter or any other electrical meter. Similarly, any current meter shown in any of the figures may be a voltage meter or other electrical meter. The tops of the devices may be substantially planar. For example, the tops of the devices may not form part of a curved surface of a cylinder, such as that in a nanopore tunnel junction.

In other embodiments, the tunneling junction may be oriented such that the side contacting the molecule is on the side of the device that is orthogonal to the insulating substrate (e.g., in FIG. 2, the side facing the viewer of the figure). With this orientation, the path of a molecule that moves left to right in FIG. 2 and along the surface of the insulating substrate may generate a tunneling current in multiple devices. This possible path is shown by dotted arrow 220. The surface of the insulating substrate along dotted arrow 220 may be substantially planar. For example, the surfaces of the insulating substrate may not form part of a curved surface of a cylinder. By providing measurement by multiple devices, the orientation of the devices shown in FIG. 2 provides an improvement over conventional junction devices.

In addition to the improved orientation of the devices, embodiments may include tapering the insulating layer, which may improve reliability, accuracy, and manufacturability. A tunneling junction for analyzing a molecule, such as DNA, may require an insulating layer with a thickness on the order of nanometers (e.g., 1-2 nm). Current processing technologies for vertical layers may result in sidewall roughness or other variations that have the same order of magnitude as the thickness. In some areas, the insulating layer may be thinner than 1-2 nm and may allow electrons to tunnel through, without the presence of a molecule contacting the metal layers. Additionally, even if a thin, uniform insulating layer of 1-2 nm can be fabricated, electrons may still tunnel from one metal layer to the other layer through the insulating layer, potentially across the entire surface area of the insulating layer.

This background tunneling current may make it difficult to detect when a molecule contacts the two metal layers. Tapering may allow the thickness of the insulating layer to be the thickness preferred for a tunneling junction (e.g., on the order of nanometers) only near the point of contact with the molecule. The rest of the insulating layer may have a thickness greater than the minimum thickness in areas other than at the point of contact. By tapering the insulating layer in this manner, the background tunneling current may be reduced. It is estimated that an additional 1 Angstrom of thickness reduces tunneling current by an order of magnitude. By tapering the insulating layer, the current from electrons tunneling through a molecule may be easier to detect when a background current of electrons tunneling through the insulating layer exists. Tapering the insulating layer may also reduce junction shorting through pinhole and other defects. As a result, tapering can increase the yield of a functioning device. Tapering can also effectively reduce the cross-sectional area of the junctions, thereby reducing the magnitude of tunneling current, and may make the structures more suitable for molecular recognition. Some embodiments may not include tapering. For example, any of the figures included may not include tapering but may include a series or array of tunneling junction devices.

Such devices may allow for manufacturing methods that are improved over methods for conventional tunneling junction devices. For example, embodiments may allow for certain fabrication steps to be performed under vacuum without exposing the junctions to the atmosphere. The junction area may also not be exposed to photoresist and reactive-ion-etch processes that may lead to contamination and shorts. Such manufacturing methods may generate high density films, and these high density films may allow fabrication of the thin junctions that are nanometer or sub-nanometer in size.

Accordingly, embodiments of the present technology may include tunneling junction devices that allow for a molecule to generate a tunneling current in multiple devices and allow for the tunneling current or other electrical characteristic to be measured reliably and repeatedly. Additional details of systems and methods are described below.

III. System of Devices

Figure 3A:
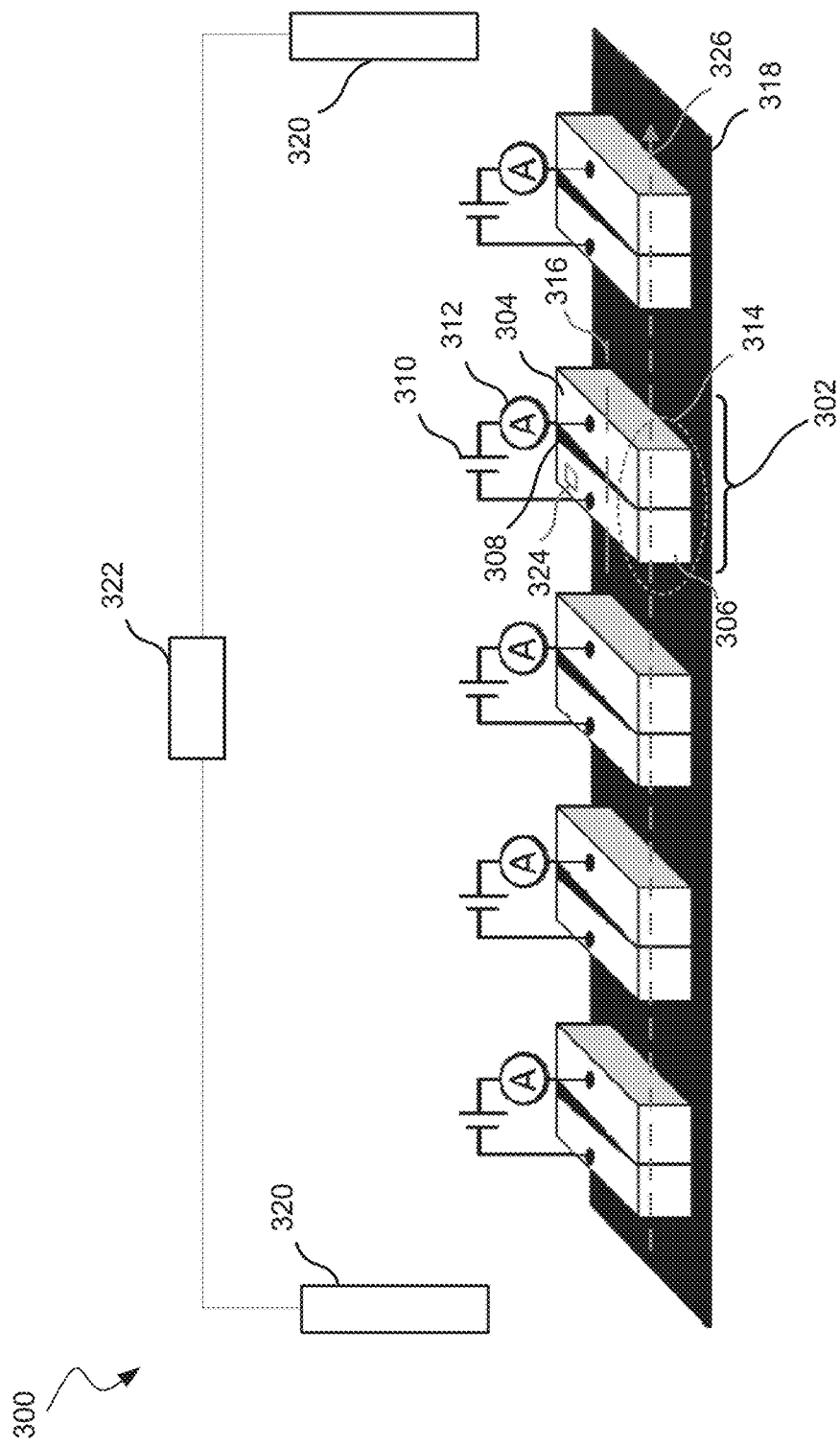
FIG. 3A shows a system of tunneling junctions that are laterally tapered according to embodiments of the present technology.

A. Arrays of Devices with Different Orientations of Tapering Insulating Material FIG. 3A shows a system 300 for analyzing a molecule according to embodiments of the present invention. System 300 includes a device 302, e.g., as part of a series of such devices. Device 302 includes a first conductive element 304 and a second conductive element 306. First conductive element 304 may include a metal, and second conductive element 306 may include a metal. The metal may include a platinum group metal, including ruthenium, rhodium, palladium, osmium, iridium, or platinum. In some embodiments, the metal may not oxidize in the presence of water or air.

Device 302 may also include an insulating layer 308 tapered in a direction to reach a minimum thickness at a first end 314 of device 302. In FIG. 3A, the direction of the taper is parallel to an edge of first conductive element 304, from the back side of device 302 hidden by the perspective in FIG. 3A to first end 314. Device 302 can be considered laterally tapered, instead of vertically tapered. As examples, the minimum thickness may be less than 1 nm, from 1 nm to 2 nm, from 2 nm to 3 nm, from 3 nm to 4 nm, from 4 nm to 5 nm, or greater than 5 nm. The taper angle may be less than or equal to 5 degrees, from 5 degrees to 10 degrees, from 10 degrees to 20 degrees, from 20 degrees to 30 degrees, from 30 degrees to 40 degrees, from 40 degrees to 45 degrees, from 45 degrees to 50 degrees, or greater than 50 degrees. A line describing a taper has a slope, a rise over run. The taper angle is the arctangent of the slope. In other words, in FIG. 3A, the taper angle is half of the angle of the triangle formed by insulating layer 308 at the vertex at first end 314. Manufacturing processes and irregularities may result in the absolute minimum thickness to be located close to but not exactly on the first end. For example, the absolute minimum thickness may be within a 1 or 2 nm of the first end, or the thickness at the first end may be within 5% or 10% of the absolute minimum thickness of the insulating layer. As insulating layer 308 is disposed between first conductive element 304 and second conductive element 306, insulating layer 308 may contact first conductive element 304 and second conductive element 306. The height of insulating layer 308 may be less than or equal to 100 nm. The area of the interface between the insulating layer 308 and a conductive element may be less than 10,000 $nm^2$. Insulating layer 308, first conductive element 304, and second conductive element 306 may each have a surface flush with the adjacent material (e.g., at least one of conductive element 304, second conductive element 306, and insulating layer 308). The surface encompassing area 324 with the tunneling junction may be substantially flat.

Insulating layer 308 may be a dielectric. As examples, insulating layer 308 may include any one or more of alumina ($Al_2O_3$), hafnia ($HfO_2$), silicon nitride ($Si_3N_4$), or silicon oxide ($SiO_2$). The insulating material may be a low-k dielectric material, which may allow for faster reading of current changes. A low-k dielectric may have a dielectric constant of less than or equal to 4.0, less than or equal to 3.9, less than or equal to 3.5, less than or equal to 3.0, less than or equal to 2.5, less than or equal to 2.0, or less than or equal to 1.5. The minimum thickness of the insulating layer may depend on the material and/or the dielectric constant. For alumina, the minimum thickness can be about 2 nm, which results in a tunneling current of about 100 pA. The minimum thickness may also depend on the molecule to be analyzed. The minimum thickness cannot be too large, otherwise the tunneling current may go through a portion of the molecule larger than the portion of interest (e.g., the tunneling current may pass through multiple nucleotides instead of a single nucleotide).

Device 302 further includes a voltage source 310 in electrical communication with first conductive element 304 and second conductive element 306. In addition, device 302 includes a current meter 312 in electrical communication with voltage source 310, first conductive element 304, and second conductive element 306. As examples, voltage source 310 may provide voltages from 0 to 1 V, including from 10 mV to 100 mV, from 100 mV to 200 mV, from 200 mV to 300 mV, from 300 mV to 500 mV, or from 500 mV to 1 V. In some embodiments, voltage source 210 may provide currents of 0 to 30 nA, including from 1 pA to 10 pA, from 10 pA to 100 pA, from 100 pA to 1 nA, 1 nA to 10 nA, or from 10 nA to 30 nA. As examples, voltage source 310 may supply a direct current voltage, an alternating current voltage, or a different waveform (e.g., pulse, sine, square, triangle, or sawtooth). Although FIG. 3A shows multiple current meters, a single current meter may monitor individual currents for each individual device. Similarly, a single voltage source may supply voltage to a plurality of devices. In embodiments, the voltage source 310 may be configured to supply a fixed current and the voltage fluctuations are measured. In other embodiments, voltage source 310 may be configured to supply a fixed voltage and the current fluctuations are measured.

Device 302 may include a tunneling direction that is orthogonal to the direction of the taper. In other words, as viewed in FIG. 3A, the tunneling direction may be from left to right or from right to left. The tunneling direction may be parallel to an axis 316 that passes through first conductive element 304, second conductive element 306, and insulating layer 308. System 300 may include a pair of electrodes 320 powered by a power source 322 and configured to create an electric field in the tunneling direction. The electric field may drive the molecule to be analyzed in the tunneling direction. In other embodiments, system 300 may include an instrument configured to create a pressure-driven fluid flow in the tunneling direction. Such an instrument may include a pump or an impeller for creating flow in the tunneling direction. The fluid can be can be water or other suitable fluid for keeping the molecules intact while allowing movement of the molecules across the tunneling junctions.

First conductive element 304, second conductive element 306, and insulating layer 308 may be disposed on a surface of an insulating substrate 318. As examples, insulating substrate 318 may be silicon dioxide or an insulating material on top of a silicon wafer. As shown in FIG. 3A, the direction of the taper may be parallel to the surface of the insulating substrate. In particular, the direction of the taper is parallel to the surface of the insulating substrate while also being orthogonal to a path of the molecule.

System 300 may include just one device 302 or may include a plurality of devices similar to device 302 in an array. The array may be configured such that a molecule to be analyzed contacts a plurality of devices when driven by an electric field or a pressure-driven fluid flow orthogonal to the direction of the taper. In FIG. 3A, the molecule can flow across the array of devices 302 along path 326 so as to contact first end 314 and the respective first ends of other devices in the array. In other words, the array would be arranged so that the molecule could move from device to device when the molecule moves along a straight path. In some embodiments, the devices may be aligned so that the respective first ends of each device are along the same line. In other embodiments, the devices may not lie on the same line, but may each be offset from a line by the same distance so that the molecule may have to wind through the devices (e.g., as described later with FIG. 5). To help with movement of a molecule, an insulating material may be deposited between devices and patterned to allow a molecule to move along a certain path. For example, a trench or channel may be formed with a sidewall of the trench including the tunneling junction areas.

System 300 may include a device submerged in a liquid used in microfluidic applications. The liquid may facilitate flow of a molecule. The liquid may include water.

Figure 3B:
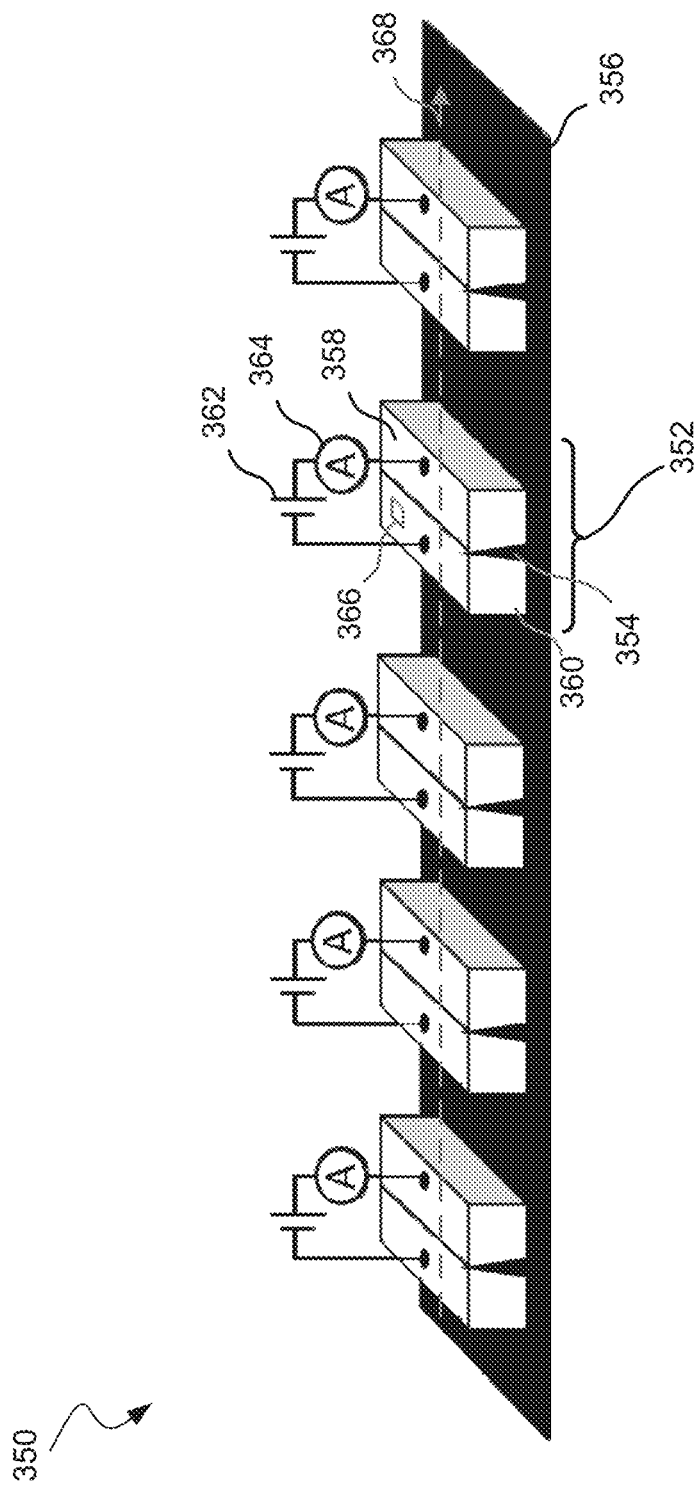
FIG. 3B shows a system of tunneling junctions that are vertically tapered according to embodiments of the present technology.

FIG. 3B shows a device 352 where the direction of the taper of insulating material 354 is orthogonal to the surface of an insulating substrate 356 according to embodiments of the present invention. The taper in FIG. 3B can be considered vertically tapered. Insulating material 354 is between a first conductive element 358 and a second conductive element 360. Insulating material 354 may be tapered to reach a minimum thickness at a first end of device 352. The first end of device 352 is the side of device 352 that includes area 366. The end may be at the top of device 352 or at an end farthest from insulating substrate 356. Device 352 further includes a voltage source 362 and a current meter 364. Insulating material 354, insulating substrate 356, first conductive element 358, second conductive element 360, voltage source 362, and current meter 364 may be any like component described herein, including those described with FIG. 3A. With FIG. 3B, a molecule to be analyzed would move either left to right or right to left (as viewed in FIG. 3B) over the top of the devices, making contact with the top surfaces of one or more of the devices. Path 368 is a possible path of a molecule to be analyzed. An additional insulating material may be added to fill in the trenches between tunneling junction devices so that a molecule may travel over a substantially flat surface.

B. Devices without a Tapered Insulating Material

Figure 4A:
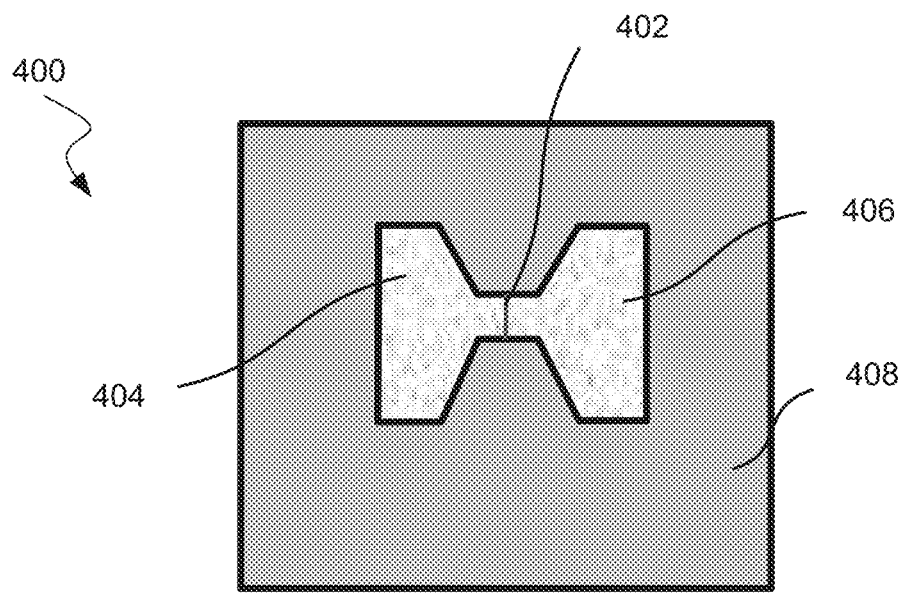
FIG. 4A and FIG. 4B show views of a tunneling junction without a taper according to embodiments of the present technology.
Figure 4B:
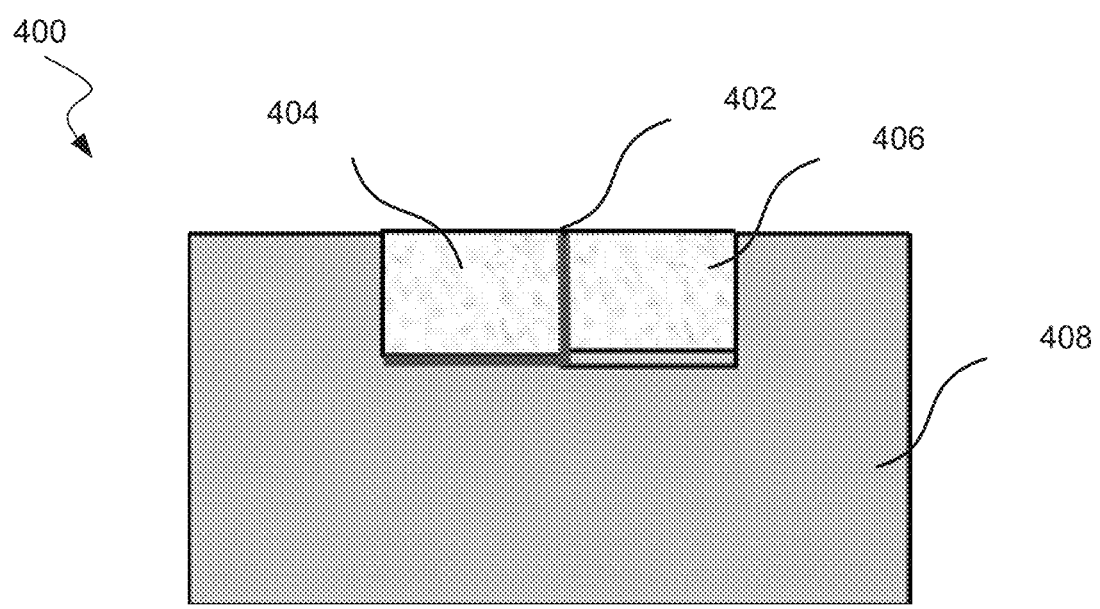

FIG. 4A and FIG. 4B show different views of device 400 without a tapered insulating material according to embodiments of the present invention. FIG. 4A shows a top view, and FIG. 4B shows a cross-sectional view. Insulating material 402 is between a first conductive element 404 and a second conductive element 406. The width (in the horizontal direction in FIG. 4A and FIG. 4B) of insulating material 402 may be kept short to reduce tunneling current and risk of defects without introducing a taper. First conductive element 404 and second conductive element 406 may increase in width and size from the interface with insulating material 402. The final shape, as viewed from the top, may be a butterfly-like shape. The increased size of the conductive elements can reduce risk of the conductive elements delaminating from insulating material 402. The top surfaces of insulating material 402, first conductive element 404, and second conductive element 406 may be substantially planar with an insulating layer 408. Insulating layer 408 may include an insulating substrate, which may be any substrate described herein, and a material deposited on top of the insulating substrate. With the top surfaces of insulating material 402, first conductive element 404, second conductive element 406, and insulating layer 408 substantially planar, a molecule can move and contact a plurality of devices along an even surface, reducing the probability that the molecule may get stuck or delayed between devices. FIGS. 4A and 4B show an orientation of the insulating layer that is rotated from the orientation for conventional tunneling junction devices in the magnetic media industry in FIG. 1. In some embodiments, insulating material 402 may be tapered as described herein.

C. Flow Path to Linearize Molecule

Figure 5:
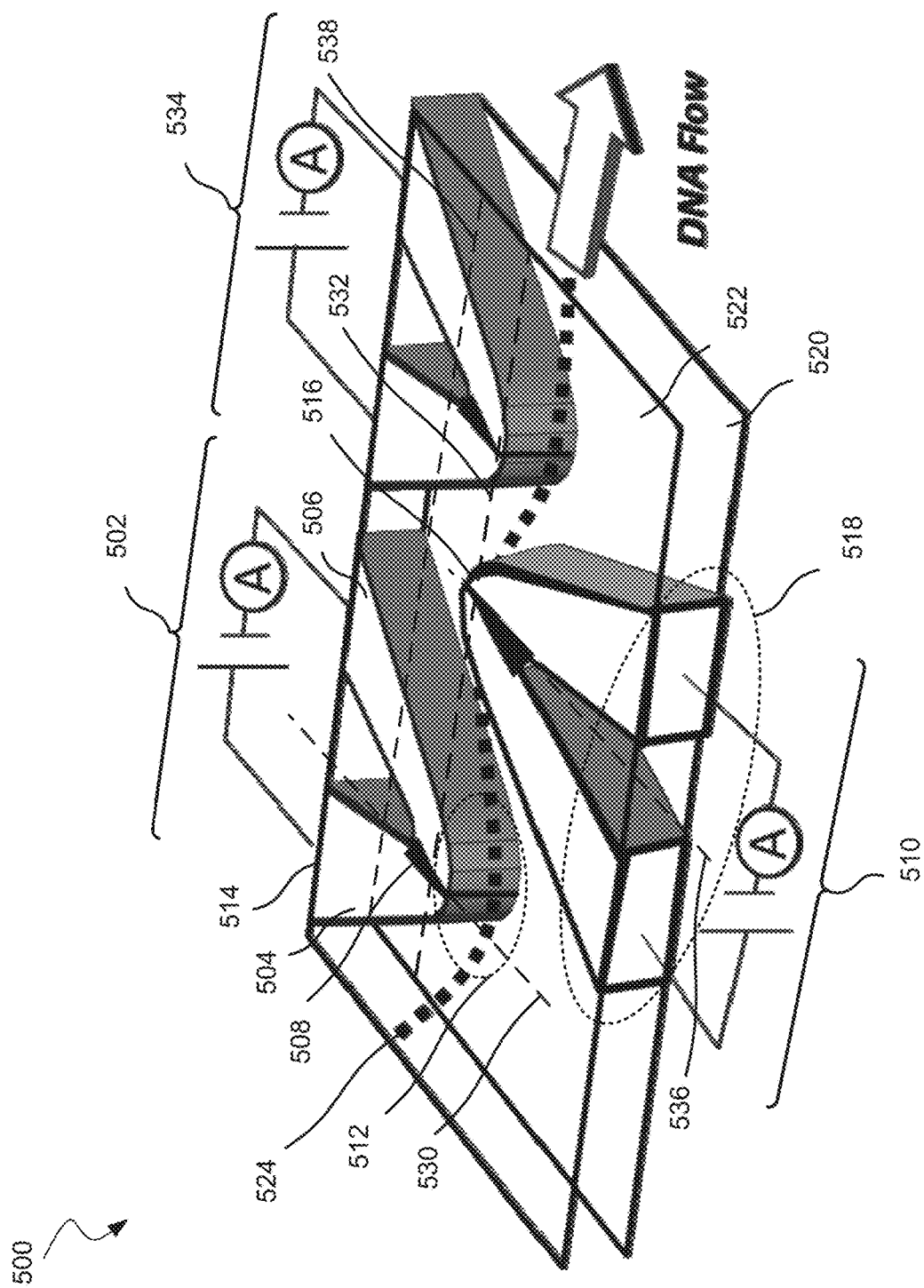
FIG. 5 shows a system of laterally tapered tunneling junctions according to embodiments of the present technology.

FIG. 5 shows a system 500 for analyzing a molecule illustrating flow of a molecule according to embodiments of the present invention. System 500 includes a first device 502. First device 502 may have a first conductive element 504 and a second conductive element 506, where each are tapered in the same direction as the direction of the taper of an insulating layer 508. In FIG. 5, device 502 has a lateral taper not a vertical taper. System 500 also includes a second device 510 identical to first device 502.

First device 502 has a first end 512, where the insulating layer 508 is at a minimum thickness, and a second end 514 opposite first end 512. Second device 510 has a first end 516, where the insulating layer is at a minimum thickness, and a second end 518 opposite first end 516. First end 512 of first device 502 may be closer to first end 516 of second device 510 than second end 514 of second device 510. Similarly, first end 516 of second device 510 may be closer to first end 512 of first device 502 than second end 514 of first device 502. The first ends may be said to face each other even though they are not aligned along an axis defined by the direction of the taper. The distance between the between first device 502 and second device 510 may be measured based on the axis in the direction of the taper without considering distances in a direction perpendicular to that axis. No other device may be between first device 502 and second device 510. In some embodiments, insulating layer 508 may not be tapered.

At the second end of each device, first conductive element 504 and second conductive element 506 may not be separated by insulating layer 508. Instead, first conductive element 504 and second conductive element 506 may be separated by a gap of air, liquid, or other fluid instead of a solid. In some embodiments, first conductive element 504 and second conductive element 506 may be separated by a solid insulating material different from the material in insulating layer 508. Device 502 and device 510 may be sandwiched between an insulating substrate 520 and an insulating surface 522. As examples, insulating surface 522 may be a dielectric, such as silicon oxide, aluminum oxide, hafnium oxide, or silicon nitride. First conductive element 504, second conductive element 506, insulating layer 508, insulating substrate 520, and insulating surface 522 may include any material described herein. In some embodiments, first conductive element 504 and second conductive element 506 may be separated by insulating layer 508 at the second end of each device.

First device 502 may be characterized by a first plane through insulating layer 508. The first plane is not shown in its entirety in FIG. 5 to maintain clarity. The first plane may include dashed line 530 and may be orthogonal to insulating substrate 520. The first plane may intersect the insulating layer 508 and neither first conductive element 504 nor second conductive element 506. A second plane orthogonal to the first plane may intersect a portion of device 516. The second plane is not shown in its entirety in FIG. 5. The second plane may include dashed line 532 and may be orthogonal to insulating substrate 520. The second plane may intersect the insulating layer and the conductive elements in device 510. Second device 510 may be characterized by a third plane through the insulating layer. The third plane is not shown in its entirety in FIG. 5. The third plane may include dashed line 536 and may be orthogonal to insulating substrate 520. The second plane including dashed line 532 may be orthogonal to the third plane including dashed line 536.

FIG. 5 shows a third device 534. Third device 534 may be identical to first device 502. The second plane comprising dashed line 532 may intersect a portion of third device 534 with the conductive elements and the insulating layer.

FIG. 5 shows a possible path 524 for the flow of a linear molecule (e.g., DNA) through system 500, e.g., by going between device 502 and device 510. The flow of DNA may be driven by electrophoresis or a pressure gradient. Path 524 can allow for the molecule to contact devices and register a tunneling current or electrical characteristic in the devices. The winding path may help keep the molecule from coiling up or from being snagged by a single device. Device 502 and device 510 may be oriented close enough to each other to force the molecule to travel through the flow channel as a linear molecule. In this manner, device 502 and device 510 can be manufactured to be separated by nanometers or less than a nanometer. Nanopores or arrays of nanopore devices with pores having sub-nanometer sizes may not be easily manufactured. Although FIG. 5 shows DNA flow, the flow can apply to other molecules to be analyzed.

In other words, the devices may be configured such that they oppose each other to form a flow channel through which the molecule moves in a linear form during an analysis operation. First device 502 and second device 510 may be offset from each other and still overlap with each other in one dimension. First device 502 and third device 534 may be aligned in at least one dimension. A plane including dashed line 538 may be orthogonal to the plane comprising dashed line 530. The plane including dashed line 538 may intersect at least one of the first conductive element 504, second conductive element 506, and insulating layer 508. As shown in FIG. 5, dashed line 538 intersects first conductive element 504 and second conductive element 506. The plane including dashed line 538 may not intersect device 510.

Each device may include an electrical meter in electrical communication with the conductive elements of the device. Each device may include a voltage source in electrical communication with the conductive elements of the device. Each device may have a separate voltage or source, or the same voltage source may be in electrical communication with multiple devices.

In embodiments, a device or an array of devices may be controlled by a computer. The computer may be any type of computing instrument including or controlling test equipment (including voltmeters, current meters, etc.). The computer may include or be coupled to an input and an output instrument coupled to the devices discussed herein.

IV. Methods of Analyzing Molecules

Figure 6:
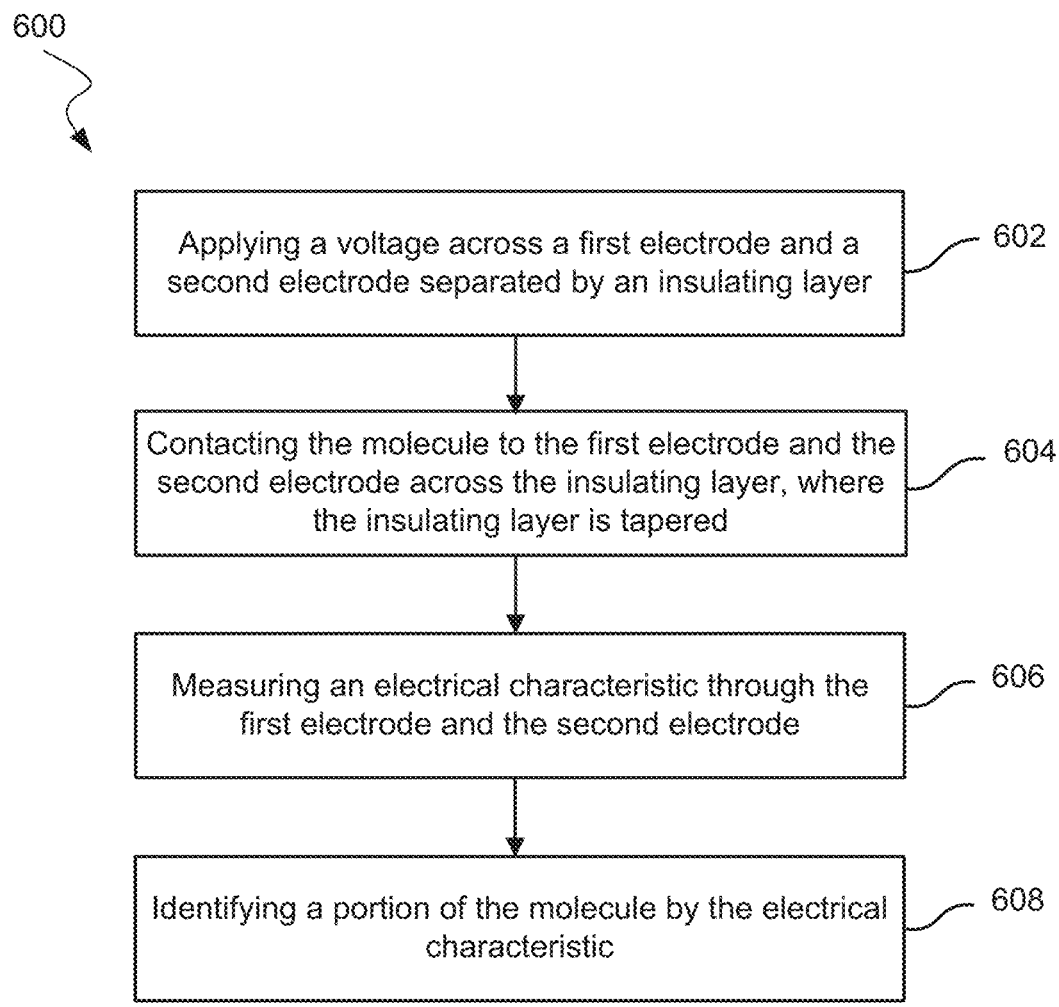
FIG. 6 shows a method of analyzing a molecule according to embodiments of the present technology.

FIG. 6 shows a method 600 of analyzing a molecule. As examples, the molecule may be a monomer, a biological polymer, a nucleic acid, or a polypeptide. Biological polymers may include carbohydrates and polysaccharides. Polypeptides include proteins. Analyzing a molecule may include identifying the molecule or identifying a portion of the molecule. With nucleic acids, analyzing the nucleic acid may include identifying nucleotides of a portion of the nucleic acid. With polypeptides, analyzing the polypeptide may include identifying amino acids in the polypeptide. Analyzing a biological polymer may include identifying a monomer unit of the polymer.

At block 602, method 600 includes applying a voltage across a first electrode and a second electrode separated by an insulating layer. Examples of devices including these electrodes and the insulating are described above. A power supply, including a voltage source, may apply the voltage. The power supply may be controlled by a computer system.

Method 600 may include moving the molecule to the first electrode and the second electrode by electrophoresis or a pressure-driven flow. Electrophoresis may be induced by applying a voltage across a pair of electrodes as described herein. A pressure-driven flow may be by a pump, impeller, or other suitable instrument. Movement of the molecule may be controlled in part by a computer, through control of electrodes or the pump or impeller.

At block 604, method 600 includes contacting the molecule to the first electrode and the second electrode across the insulating layer. The insulating layer can be tapered such that the end of the insulating layer closest to the molecule includes the minimum thickness of the insulating layer. Such tapering is described above, e.g., with respect to FIGS. 3A, 3B, and 5.

At block 606, method 600 includes measuring an electrical characteristic through the first electrode and the second electrode. A change in electrical characteristic may be determined relative to a background electrical characteristic. The electrical characteristic may be measured by an electrical meter, which may take various forms, as will be appreciated by one skilled in the art. Electrical characteristics include current, voltage, and any other characteristic described herein. The measurement may be received by a computer system.

At block 608, method 600 may include identifying a portion of the molecule based on the measured electrical characteristic. Identifying a portion of the molecule may include identifying the presence or absence of a part of a sequence of the molecule (e.g., a nucleotide or an amino acid) or a functional group. Identifying the portion of the molecule may include comparing the measured electrical characteristic or change in electrical characteristic against a reference value or a calibration value. The electrical characteristic may be current, voltage, or any characteristic described herein. For example, each of the four nucleotides of DNA or each of the 20 amino acids of proteins may have a current or change in current previously characterized. Distinguishing different portions of the molecule may use current differences on the order of tens of picoamps. The calibration current or reference current may be based on a plurality of readings. For example, the reference current may be based on hundreds, thousands, or tens of thousands of current measurements across the device or similar devices. Such measured values can be averaged, and the average can be compared to a reference or calibration value. Other statistical values besides a mean average can be used, e.g., a median or mode. Identification of the portion of the molecule may use a computer system. The computer system may have reference currents or other electrical characteristics stored within the system.

Method 600 may include a second tunneling junction device, e.g., as part of an array of devices, as mentioned above. Method 600 may include applying a voltage across a third electrode and a fourth electrode, which are separated by a second insulating layer. Method 600 may further include moving the molecule from the first electrode and the second electrode to the third electrode and the fourth electrode. In addition, method 600 may include contacting the molecule to the third electrode and the fourth electrode across the second insulating layer. The second insulating layer may be tapered such that the second insulating layer is at a minimum thickness at the end of the second insulating layer closest to the molecule. Method 600 may include measuring an electrical characteristic through the third electrode and the fourth electrode.

Method 600 may further include comparing the electrical characteristic through the third electrode and the fourth electrode to the electrical characteristic through the first electrode and the second electrode. Comparing the electrical characteristics may include averaging electrical characteristic values (average may include mean, median, or mode), performing other statistical functions (e.g., calculating standard deviation, t-test), or plotting the current values. Comparing the electrical characteristic may use a computer system. Method 600 may include contacting the molecule to a plurality of devices. The plurality may include from 50 to 100, from 100 to 500, from 500 to 1,000, from 1,000 to 5,000, from 5,000 to 10,000, or over 10,000 devices. A statistical test may be used to determine if the electrical characteristic distribution from a portion of the molecule is the same or different from reference electrical characteristic.

In some embodiments, methods may include flowing a molecule through a flowpath formed by offset and overlapping devices as described herein with FIG. 5.

V. Methods of Manufacturing

Figure 7:
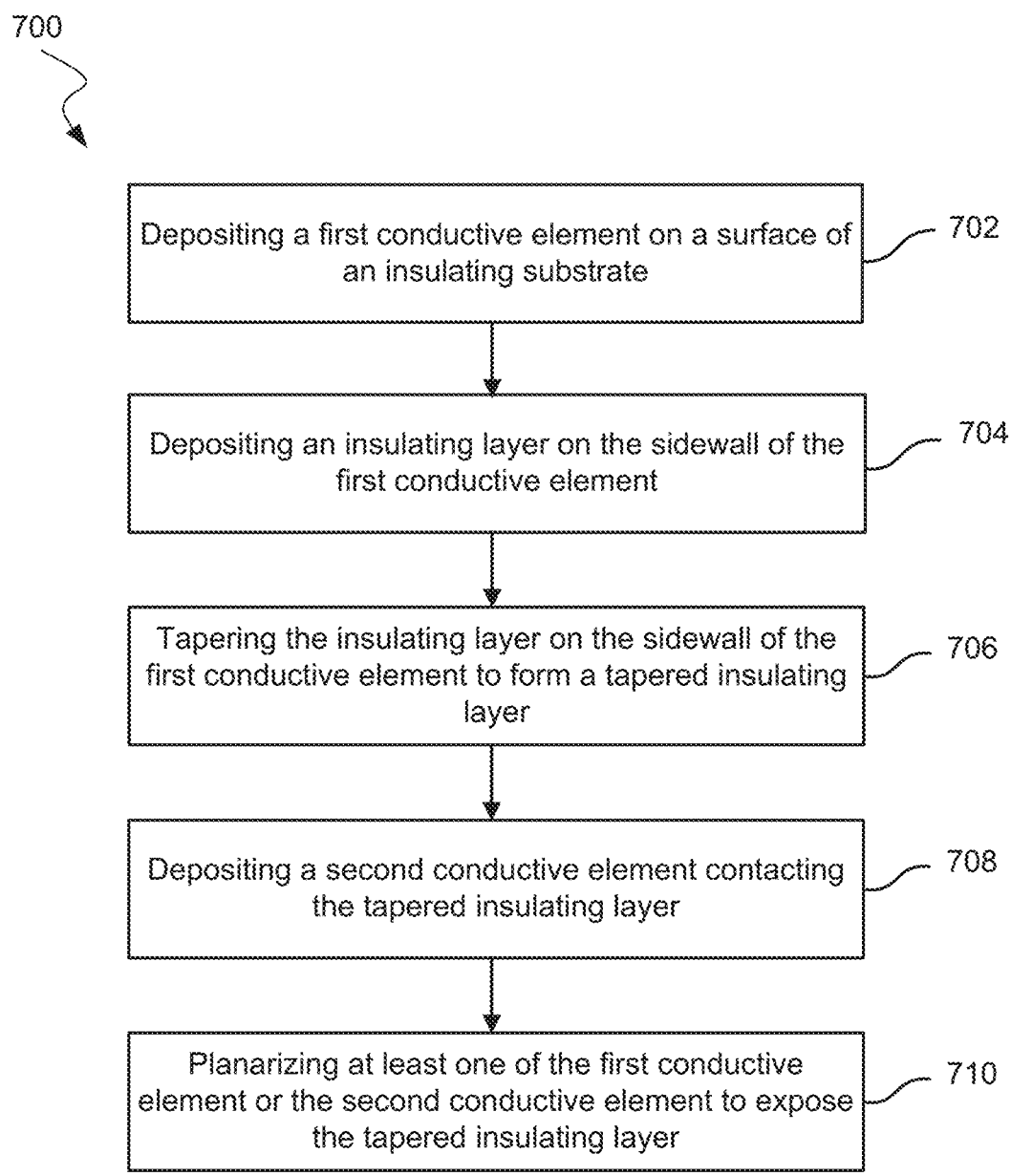
FIG. 7 shows a method of manufacturing a device for analyzing a molecule according to embodiments of the present technology.

FIG. 7 shows a method 700 of manufacturing a device for analyzing a molecule. Manufacturing methods may include techniques used with manufacturing magnetic recording media (e.g., magnetic hard drives).

At block 702, method 700 includes depositing a first conductive element on a surface of an insulating substrate. The first conductive element may be deposited by ion beam deposition. Ion beam deposition may result in a denser film compared to other techniques. The first conductive element may be patterned to the target dimensions by suitable patterning techniques.

At block 704, method 700 includes depositing an insulating layer on the sidewall of the first conductive element. The insulating layer may be deposited by ion beam deposition (IBD) or atomic layer deposition (ALD). The insulating layer may be deposited conformally over the first conductive element.

At block 706, method 700 includes tapering the insulating layer on the sidewall of the first conductive element to form a tapered insulating layer. Tapering the insulating layer may include tapering the insulating layer in a direction orthogonal to the surface of the insulating substrate (i.e., a vertical taper). In other embodiments, tapering the insulating layer may include tapering the insulating layer in a direction parallel to the surface of the insulating substrate (i.e., a lateral taper). Tapering the insulating layer may include ion beam etching of the insulating layer at an angle (e.g., ion beam with argon ions at a 45 degree angle). The tapering may be aided by shadowing of the sidewall provided by the adjacent feature patterned in the first conductive element. For example, the adjacent feature may form a trench with the sidewall of the first conductive element, and the trench may shadow part of the insulating layer on the sidewall to aid in tapering.

In some embodiments, depositing the insulating layer may be shadowed by another structure, and the insulating layer as deposited may be tapered instead of conformal over the first conductive element. As a result, the method may reduce the tapering through an etching operation or the method may eliminate the tapering operation entirely.

At block 706, method 700 include depositing a second conductive element contacting the tapered insulating layer. The second conductive element may be deposited with IBD or ALD.

At block 710, method 700 includes planarizing at least one of the first conductive element or the second conductive element to expose the tapered insulating layer. Planarizing may be by chemical mechanical planarization or ion beam etching.

Method 700 may further include connecting the first conductive element and the second conductive element to a voltage source and an electrical meter. Electrically connecting the first conductive element and the second conductive element to the voltage source or electrical meter may include metal pads or contacts and other metal processing techniques known in magnetic recording media manufacturing.

A. Example Method of Forming Vertical Taper

Figure 8A:
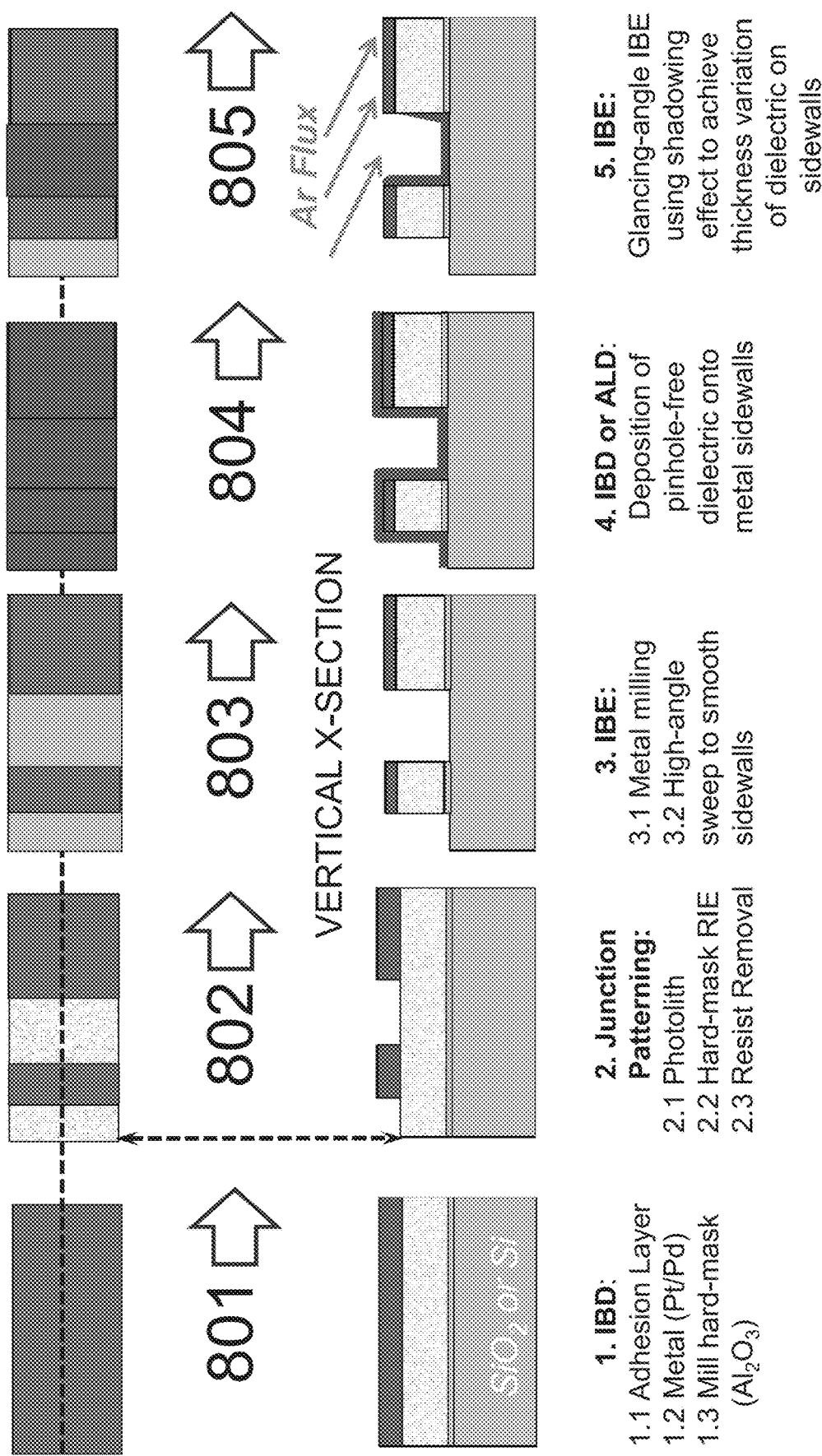
FIG. 8A and FIG. 8B show an example method of manufacturing vertically tapered tunneling junction devices according to embodiments of the present technology.

FIG. 8A shows an example of forming a vertically tapered tunneling junction device. In section 801, an adhesion layer, a metal, and a hard mask are deposited by ion beam deposition (IBD). The adhesion layer is deposited on top of $SiO_2$ or Si. The metal (e.g., platinum or palladium) is deposited on top of the adhesion layer. The hard mask is deposited on top of the metal. In section 802, junctions are patterned with photolithography, hard-mask reactive ion etch (RIE), and resist removal. In section 803, ion beam etching (IBE) is done to mill the metal and to smooth sidewalls. In section 804, a dielectric layer is deposited by ion beam deposition (IBD) or atomic layer deposition (IBD). In section 805, the dielectric on the sidewalls is tapered using IBE and a shadowing effect.

Figure 8B:
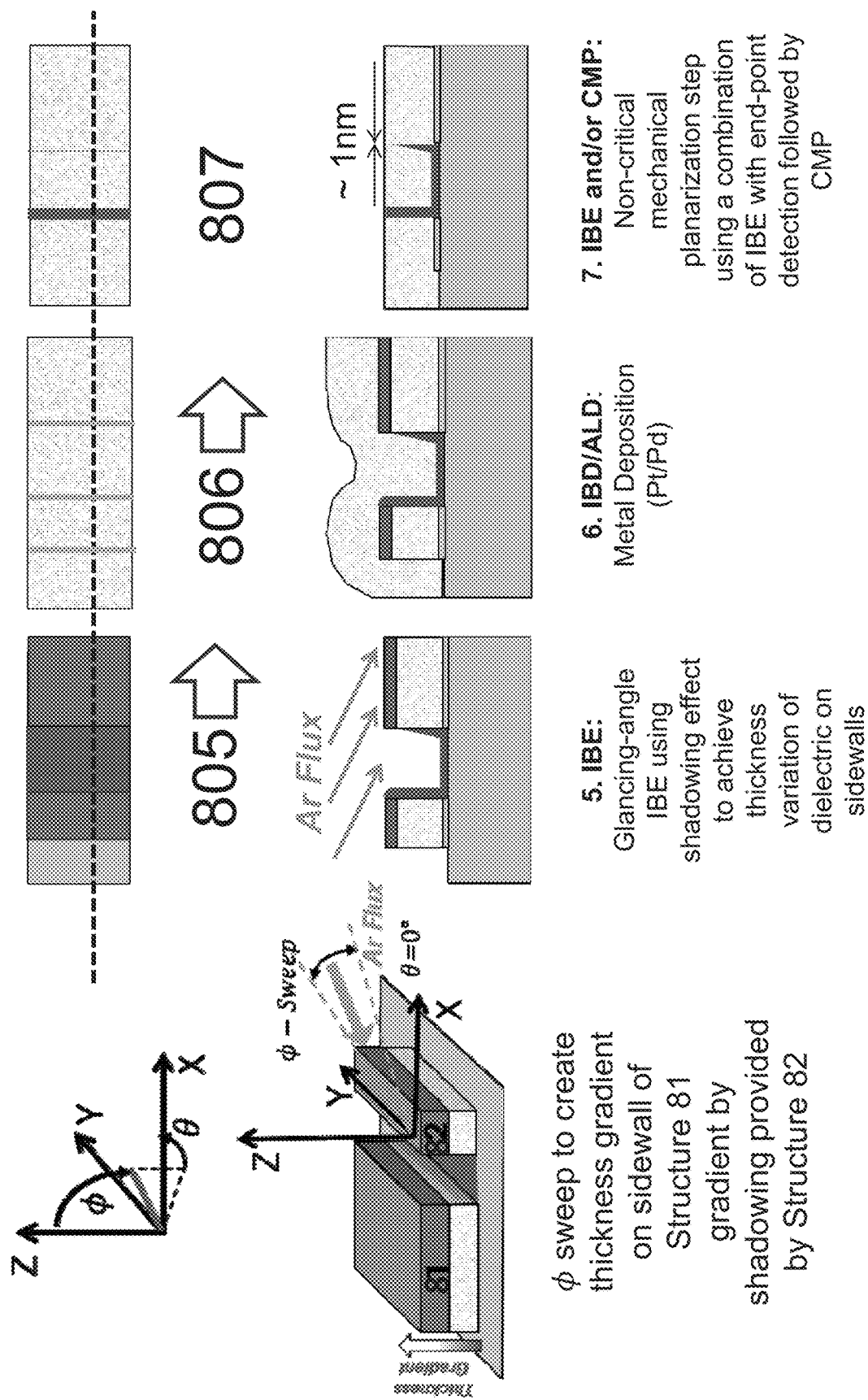

FIG. 8B shows additional detail on tapering in section 805 and additional steps in processing, following FIG. 8A. Structure 82 may be used to shadow structure 81. The structure used to shadow the sidewall may be aligned with the structure having sidewall targeted to be tapered. A flux of ions, including those from argon, may be introduced at an angle non-normal and non-parallel relative to the surface of the substrate. The flux of ions may be swept in the XZ plane (direction) to create the thickness gradient. Some of the ions are blocked by structure 82 before the ions reach the sidewall of structure 81. More ions that would otherwise be headed toward the bottom of structure 81 are blocked than ions that are headed to toward the top of structure 81. As a result, more of the dielectric is etched away from the top of structure 81 compared to the bottom of structure 81, resulting in a taper in the dielectric. In section 806, a metal is deposited by IBD or ALD. This metal may eventually form the second electrode of the device. In section 807, IBE or chemical mechanical planarization (CMP) is used to expose the minimum thickness of the tapered dielectric.

B. Example Method of Forming Lateral Taper

Figure 9A:
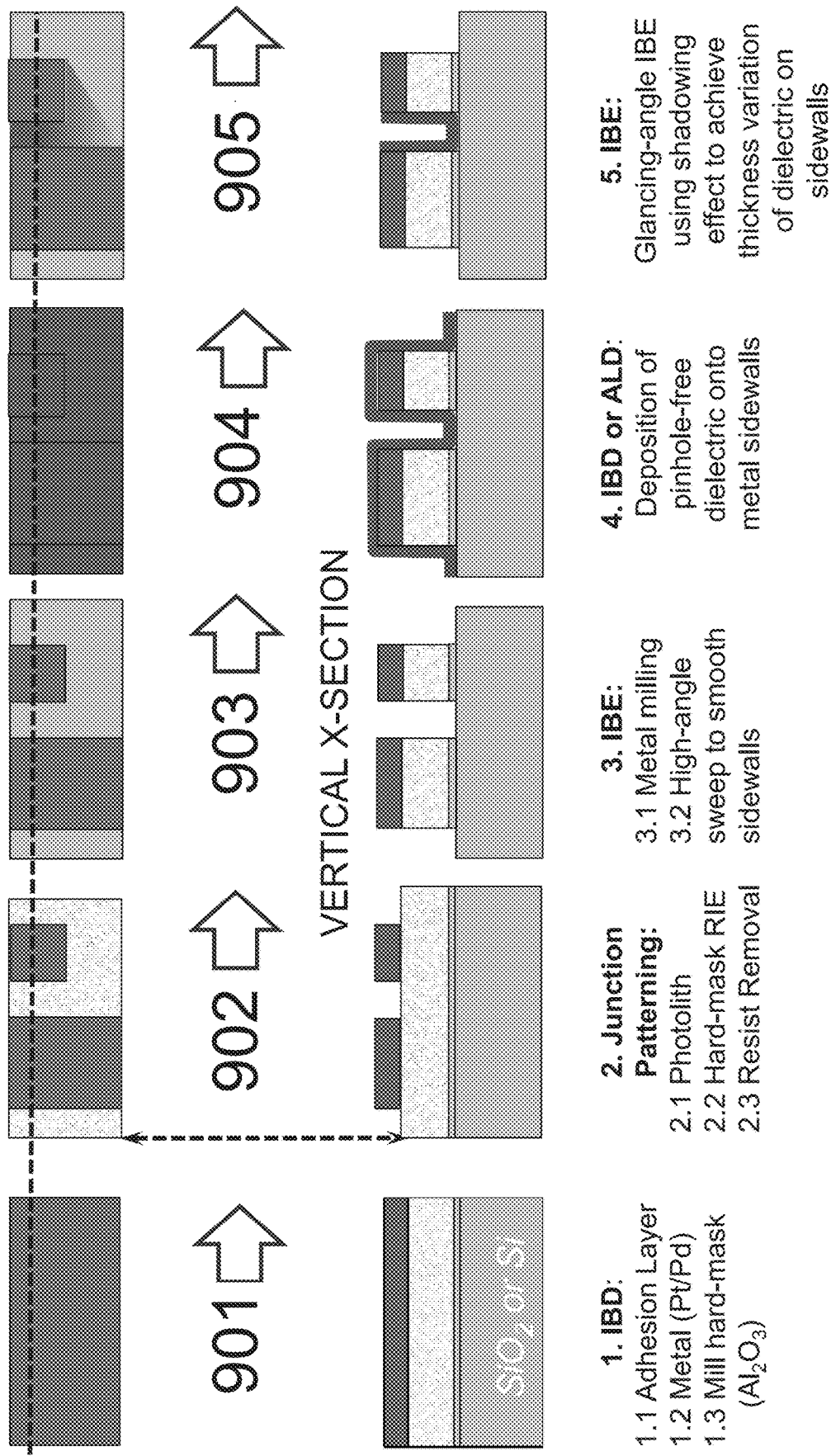
FIG. 9A and FIG. 9B show an example method of manufacturing laterally tapered tunneling junction devices according to embodiments of the present technology.

FIG. 9A shows an example of forming a laterally tapered tunneling junction device. In section 901, an adhesion layer, a metal, and a hard mask are deposited by ion beam deposition (IBD). The adhesion layer is deposited on top of $SiO_2$ or Si. The metal (e.g., platinum or palladium) is deposited on top of the adhesion layer. The hard mask is deposited on top of the metal. In section 902, junctions are patterned with photolithography, hard-mask reactive ion etch (RIE), and resist removal. In section 903, ion beam etching (IBE) is done to mill the metal and to smooth sidewalls. In section 904, dielectric layer is deposited by ion beam deposition (IBD) or atomic layer deposition (IBD). In section 905, the dielectric on the sidewalls is tapered using IBE and a shadowing effect.

Figure 9B:
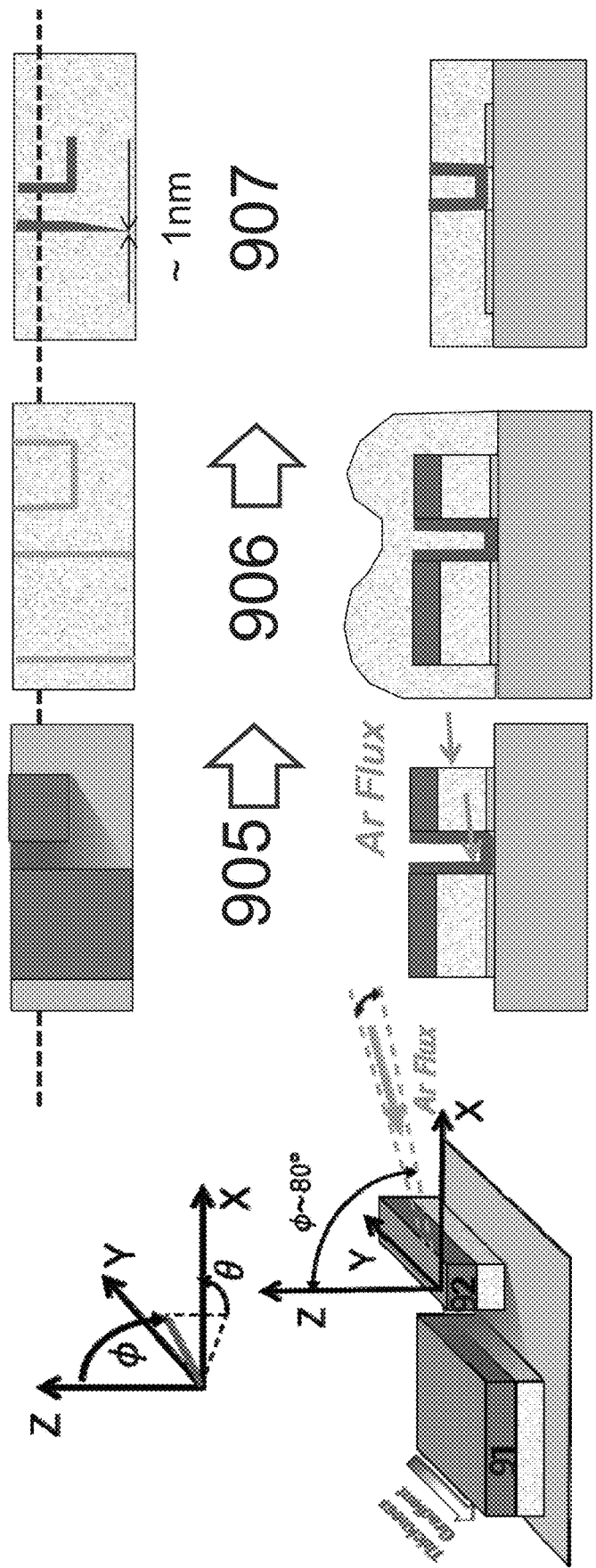

FIG. 9B shows additional detail on tapering in section 905 and additional steps in processing, following FIG. 9A. The argon flux angle and the shadowing is different from FIG. 9B. To create a lateral taper, a structure offset from the sidewall to be tapered is used for shadowing, while in FIG. 8B, the structure used for shadowing is aligned to the sidewall. In FIG. 9B, structure 92 is offset from structure 91 and shadows structure 91. A flux of ions, including those from argon, may be introduced at an angle φ that may be non-normal or non-parallel relative to the surface of the substrate. The ions may be swept in the XY plane to create the thickness gradient. Some of the ions are blocked by structure 92 before the ions reach the sidewall at one end of structure 91 closest to the center of mass of structure 92. More ions that would otherwise be headed toward the end of structure 91 are blocked than ions that are headed to toward structure 91 but farther from the end. As a result, more of the dielectric is etched away from the end of structure 91, resulting in a taper in the dielectric. In section 906, a metal is deposited by IBD or ALD. This metal may eventually form the second electrode of the device. In section 907, IBE or chemical mechanical planarization (CMP) is used to expose the minimum thickness of the tapered dielectric.

VI. Computer System

Figure 10:
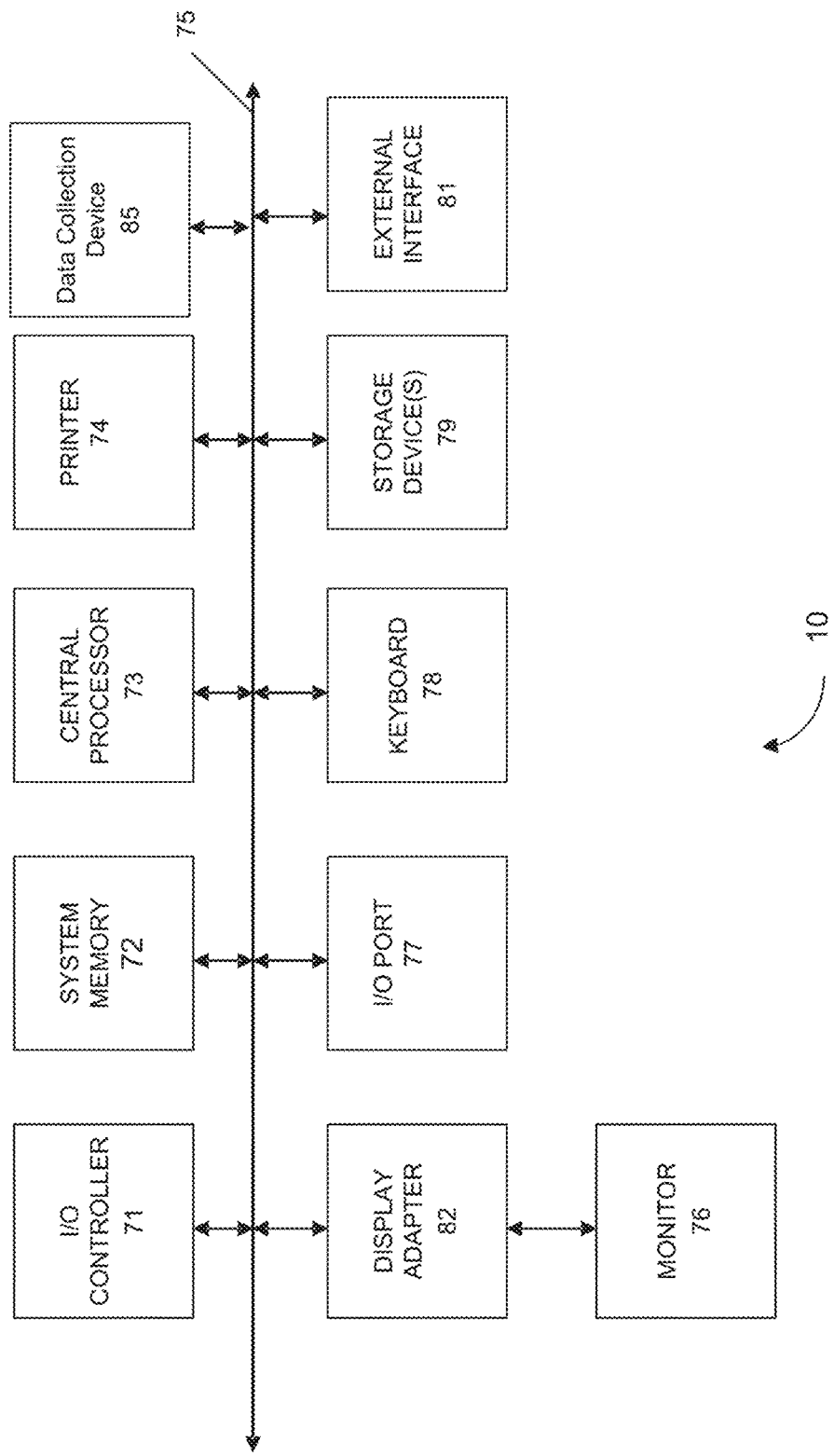
FIG. 10 shows a computer system according to embodiments of the present technology.

Any of the computer systems mentioned herein may utilize any suitable number of subsystems. Examples of such subsystems are shown in FIG. 10 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 10 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®, Thunderbolt). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

Figure 11:
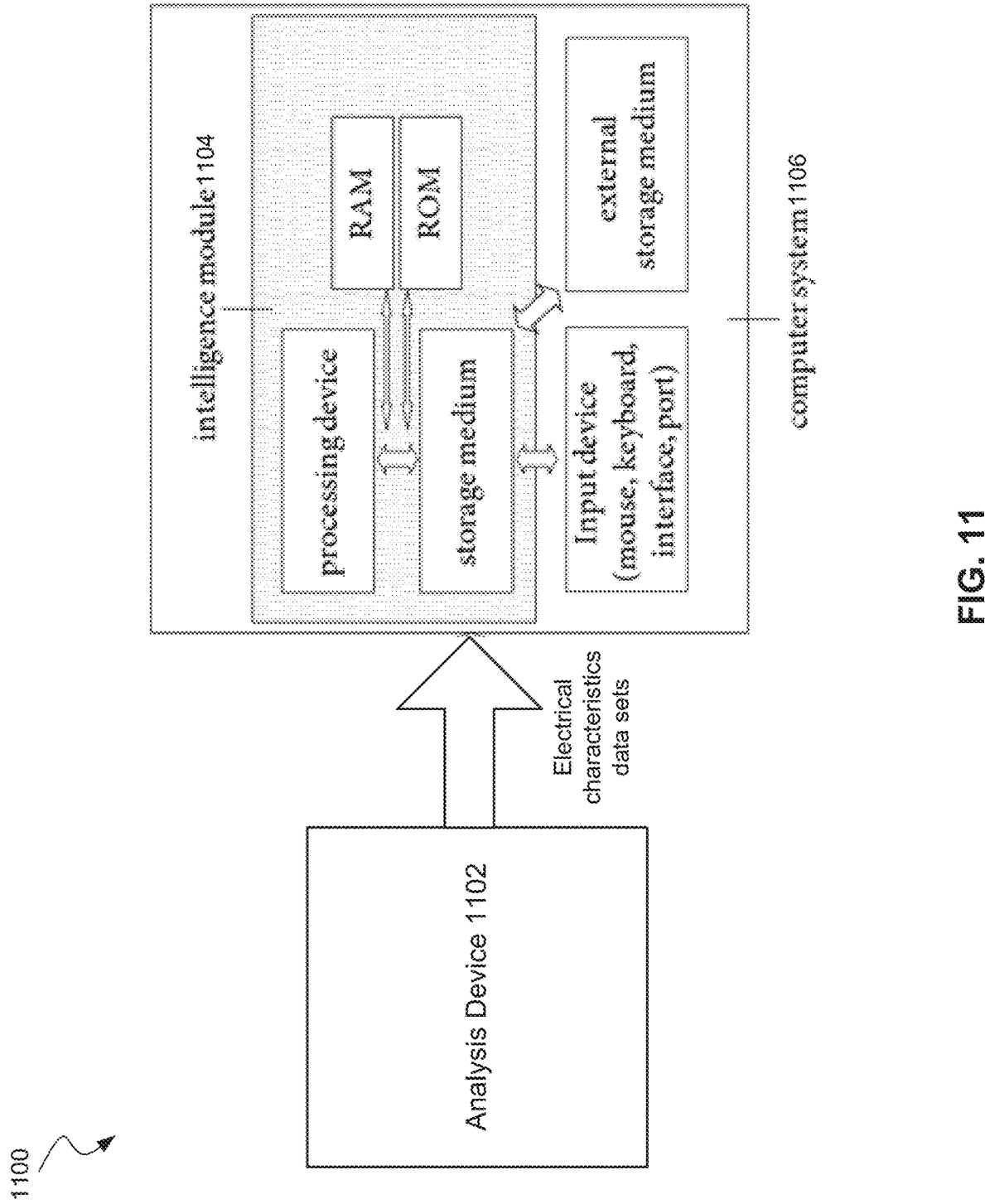
FIG. 11 shows an analysis system according to embodiments of the present technology.

FIG. 11 shows an exemplary analysis system. The system depicted in FIG. 11 comprises an analysis device 1102 and an intelligence module 1104 which is part of the computer system 1106. Analysis device 1102 may include system 200, system 300, system 350, device 400, system 500, or any system described herein. Computer system 1106 may include parts or all of computer system 10. The data sets (electrical characteristics data sets) are transferred from the analysis device 1102 to the intelligence module 1104 or vice versa via a network connection or a direct connection. The data sets may for example be processed to identify nucleotides. The identification steps may be implemented by software stored on the hardware of computer system 1106. The data sets may be processed by computer code running on the processor and being stored on the storage device of the intelligence module and after processing transferred back to the storage device of the analysis module, where the modified data may be displayed on a displaying device. In some embodiments, the intelligence module may also be implemented in the analysis device.

Figure 12:
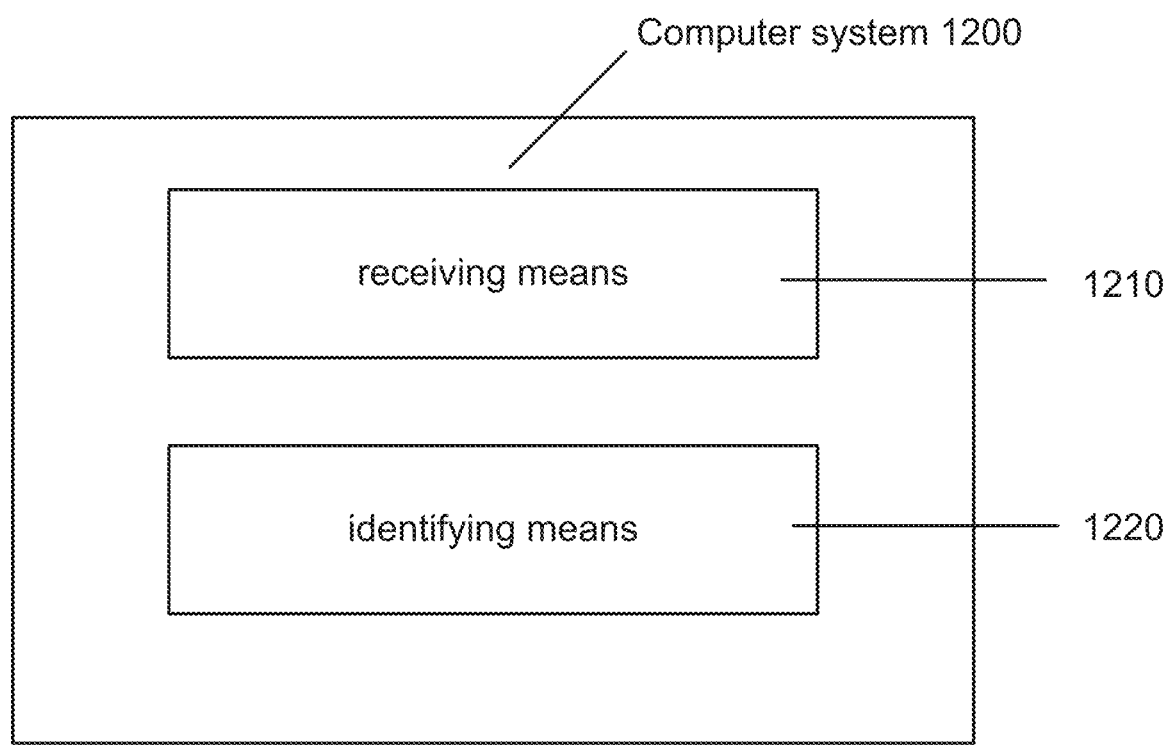
FIG. 12 shows a computer system according to embodiments of the present technology.

FIG. 12 shows that computer system 1200 may comprise receiving means 1210, which may include, for example, receiving electrical characteristic data obtained from a sequencing device. Computer system 1200 may also include identifying means 1220 for identifying a portion of a molecule causing a change in the electrical characteristic in the data.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A system for analyzing a molecule, the system comprising a device, the device comprising:
a first conductive element;
a second conductive element;
an insulating layer tapered in a direction to reach a minimum thickness at a first end of the device, the insulating layer disposed between the first conductive element and the second conductive element;

a voltage source in electrical communication with the first conductive element and the second conductive element; and an electrical meter in electrical communication with the voltage source, the first conductive element, and the second conductive element.

2. The system of claim 1, wherein:
the direction is a first direction,
further comprising:
a pair of electrodes configured to create an electric field in a second direction orthogonal to the first direction, wherein the second direction is parallel to an axis that passes through the first conductive element, and the insulating layer.

3. The system of claim 1, wherein:
the direction is a first direction,
further comprising:
an instrument configured to create a pressure-driven fluid flow in a second direction orthogonal to the first direction, wherein the second direction is parallel to an axis that passes through the first conductive element, the insulating layer, and the second conductive element.

4. The system of claim 1, wherein the first conductive element comprises a metal, the second conductive element comprises a metal, and the insulating layer is a dielectric.

5. The system of claim 1, wherein the insulating layer comprises alumina, hafnia, silicon nitride, or silicon oxide.

6. The system of claim 1, wherein:
the first conductive element, the second conductive element, and the insulating layer are disposed on a surface of an insulating substrate, and
the direction is orthogonal to the surface of the insulating substrate.

7. The system of claim 1, wherein:
the first conductive element, the second conductive element, and the insulating layer are disposed on a surface of an insulating substrate, and
the direction is parallel to the surface of the insulating substrate.

8. The system of claim 1, further comprising a plurality of devices in an array that includes the device.

9. The system of claim 8, wherein the array is configured such that the molecule contacts the plurality of devices when driven by an electric field or a pressure-driven fluid flow orthogonal to the direction.

10. The system of claim 1, wherein:
the device is a first device,
the system comprises a second device identical to the first device,
the first device comprises a second end opposite the first end of the first device,
the second device comprises a second end opposite the first end of the second device, and
the first device and the second device are disposed on a surface of an insulating substrate such that:
the first end of the first device is closer to the first end of the second device than the second end of the second device, and
the first end of the second device is closer to the first end of the first device than the second end of the first device.

11. The system of claim 1, wherein:
the first conductive element and the second conductive element are each tapered such that the maximum thickness of each element is not at the first end,
the first conductive element and the second conductive element are not separated by the insulating layer at a second end opposite the first end.

12. The system of claim 1, further comprising a liquid, wherein a portion of the device is submerged in the liquid.

* * * * *